United States Patent [19]

Lee

[11] Patent Number: 4,857,318

[45] Date of Patent: Aug. 15, 1989

[54] BORDETELLA BRONCHISEPTICA PILUS SUBUNIT PROTEIN VACCINE EFFECTIVE AGAINST BORDETELLA PERTUSSIS

[75] Inventor: Simon W. Lee, San Jose, Calif.

[73] Assignee: Syntex (U.S.A.) Inc., Palo Alto, Calif.

[21] Appl. No.: 715,805

[22] Filed: Mar. 25, 1985

Related U.S. Application Data

[63] Continuation-in-part of Ser. No. 549,384, Nov. 7, 1983, abandoned.

[51] Int. Cl.⁴ ...................... C12P 21/00; A61K 39/00; C07G 7/00

[52] U.S. Cl. ........................................ 424/92; 424/88; 530/350; 530/395; 514/2; 514/8; 435/68

[58] Field of Search .................... 424/88, 92; 435/253, 435/822, 68; 530/350; 514/2, 8

[56] References Cited

U.S. PATENT DOCUMENTS

| | | | |
|---|---|---|---|
| 3,873,691 | 3/1975 | Kasuga et al. | 424/92 |
| 4,172,125 | 10/1979 | Audibert et al. | 424/89 |
| 4,203,970 | 5/1980 | Carlo et al. | 424/92 |
| 4,337,314 | 6/1982 | Oeschger et al. | 435/253 |
| 4,452,734 | 6/1984 | Larsan et al. | 424/89 |
| 4,562,070 | 12/1985 | Wood | 424/92 |
| 4,606,918 | 8/1986 | Allison et al. | 424/88 |

OTHER PUBLICATIONS

Bemis et al., *J. Clin. Microbiol.,* vol. 15, 1120 (1982).

Berghe's, *Manual of Determinative Bacteriology,* 8th Ed., 1974, pp. 282–283.

Asworth et al., *Infect. Immun,* vol. 37, pp. 1278–1281, 1982, "Antigenic Relationship Between Serotype-Specific Agglutination and Fimbrae of *Bordetella Pertussis*".

Beachey et al., *T Infect Immun,* vol. 143, pp. 325–345, 1981, "Bacterial Adherence: Adhesion-Receptive the Attachment of Bacteria to Mucosal Surfaces".

Morgan et al., 1978, *Infec. Immn.,* vol. 22, pp. 771–777, "Immunization of Suckling Pigs Against Escherichia colii".

Shade et al., *Vet. Med. Small Anon. Clin,* vol. 77, pp. 1635–1639, 1982, "Studies of a Bacteria Incorporating an extracted . . . ".

S. Lee, *Infec. & Immun.,* 51, 586–593 (1986).

*Primary Examiner*—Robin Teskin

*Attorney, Agent, or Firm*—Carol J. Roth; Derek P. Freyberg; Tom M. Moran

[57] ABSTRACT

A vaccine derived from *Bordetalla bronchiseptica* effective against *Bordetella pertussis* infection is disclosed herein.

20 Claims, No Drawings

BORDETELLA BRONCHISEPTICA PILUS SUBUNIT PROTEIN VACCINE EFFECTIVE AGAINST BORDETELLA PERTUSSIS

This application is a continuation-in-part of pending U.S. application No. 549,384 filed Nov. 7, 1983, now abandoned.

BACKGROUND OF THE INVENTION

This invention relates to a vaccine for the prevention of Bordetella pertussis (B. pertussis) infections.

Atrophic rhinitis is a widespread and severe respiratory disease in swine. The disease is characterized by acute rhinitis, followed by chronic atrophy of the turbinate bones. Bordetella bronchiseptica (B. bronchiseptica) is recognized as the primary pathogen most responsible for the disease syndrome. Newborn piglets are very susceptible to infection. Nasal colonization of baby piglets with B. bronchiseptica usually results in chronic infection and turbinate atrophy leading to snout distortion and reduced rate of weight gain as pigs grow older.

Prevention of B. bronchiseptica induced turbinate atrophy and accelerated nasal clearance of the bacteria by vaccination of swine with a B. bronchiseptica bacterin has been reported. The nature of the immunizing antigen has not been identified. Heat-labile pilus-like surface antigens are implicated in the adherence of the bacterium to swine nasal epithelium. A pilus vaccine, like the E. coli colibaccillosis vaccine, would prevent colonization and thereby prevent infection by B. bronchiseptica.

Vaccines for B. bronchiseptica are disclosed in several literature references, for example, see U.S. Pat. No. 4,203,970 and Goodnow, et al., J. Clin. Microbiology, 6, 337–339 (1977). None of these references are drawn to a vaccine derived from pili and comprising proteins of the specific characteristics disclosed herein.

Pertussis, whooping cough, is an acute infectious disease caused by Bordetella pertussis, and characterized by recurrent bouts of spasmodic coughing continued until the breath is exhausted, ending in a noisy inspiratory stridor (the "whoop") caused by laryngeal spasm. The lesion is an inflammation of the larynx, trachea, and bronchi.

Though vaccines for pertussis derived from B. pertussis exist, there is no reported effective vaccine against pertussis based on antigenic material derived from B. bronchiseptica. Further, pertussis vaccines have been found to cause severe side effects in some individuals. It has now been discovered that materials derived from B. bronchiseptica, particularly pili proteins, are capable of imparting protection against B. pertussis infections in addition to their protective activity against B. bronchiseptica.

SUMMARY OF THE INVENTION

One aspect of the invention relates to a vaccine for immunizing a human subject against B. pertussis which comprises an effective amount of inactivated B. bronchiseptica having pili.

A second aspect of this invention is a vaccine for immunizing a human subject against B. pertussis which comprises an effective amount of substantially pure pilus subunit proteins derived from B. bronchiseptica.

This invention also relates to a composition of matter comprising a substantially pure pilus subunit protein derived from B. bronchiseptica and characterized by having a molecular weight of about 22,000 daltons as determined by sodium dodecyl sulfate-polyacrylamide gel electrophoresis and having the amino acid composition set forth below.

This invention also encompasses a method for immunizing a human subject against whooping cough, which method comprises vaccinating said human subject with a composition comprised of substantially pure pilus subunit proteins derived from B. bronchiseptica.

DEFINITIONS

As used herein, the term "immunize" refers to the ability of the subject to withstand and combat invasion and multiplication of microorganisms in body tissues. Such infections often result in local cellular injury due to competitive metabolism, toxins, intracellular replication, or antigen-antibody response. The immunological response may be transient or prolonged, and consists of a cellular response (delayed hypersensitivity) and/or the production of specific (immunoglobulin) antibodies to the components of the infecting organism or its toxins. Objects of the invention include immunizing human subjects against infection by B. pertussis.

As used herein, the term "effective amount" is that amount of B. bronchiseptica, pili, or pilus subunit proteins which is sufficient to immunize a human subject against infection. The human subject is usually a young child. The effective amount may vary, depending on the age of the subject, specific activity of the pili preparation, efficacy of the adjuvant, and other factors. However, the effective amount may be determined easily by one skilled in the art. Generally, an effective amount of purified pilus protein will range from about 0.02 μg/dose to about 40 μg/dose. A more preferred range is from about 1 μg/dose to about 20 μg/dose.

The term "inactivated" B. bronchiseptica refers to B. bronchiseptica which has been treated so that it has lost its ability to cause infection in an animal, but retains the ability to evoke an immunological response. Inactivation may be accomplished by means known in the art, such as treating the bacteria with heat or lysing agents.

DETAILED DESCRIPTION OF THE INVENTION

It has now been found that inactivated B. bronchiseptica can provide protective activity against B. pertussis. More specifically, the pili from B. bronchiseptica provide protection against infection by B. pertussis, the causative agent in whooping cough. While it is preferred to use intact, whole, substantially pure pili or subunit proteins derived therefrom, it is also possible to use whole cells which have been inactivated or killed, or pill-containing fragments of whole cells in the practice of this invention. Most preferred is a 22,000 dalton (22 Kd) pili subunit protein.

Microscopic and biochemical analyses indicate that pili from B. bronchiseptica are morphologically and structurally similar. B. bronchiseptica pili are filamentous assemblies of protein subunits. The average diameter of pili isolated and purified from various strains is about 4 nm.

The pilus-derived proteins responsible for imparting protection are obtained as a mixture of pill separated from cells and cellular debris upon treating lysed B. bronchiseptica with a precipitant. This material, the first precipitate, can be used directly without further purification to prepare a vaccine which can be characterized as a pilus subunit protein vaccine.

Depending on the growth conditions and colonial morphology of the organisms, additional purification provides three subunit proteins of three distinct molecular sizes of about 21 Kd, 22 Kd and 24 Kd as determined by sodium dodecyl sulfate-polyacrylamide gel electrophoresis (SDS-PAGE). It is preferred to use the 22 Kd protein in the practice of the invention. Two sets of standards were used to characterize these proteins, one set being the proteins K-88, K-99, and 987 p *E. coli* pilus antigens and the other set being the proteins chymotrypsinogen, lactoglobulin, trypsin inhibitor, myoglobulin, ovalbumin and bovine serum albumin.

Using hyperimmune rabbit antipilus sera in an ELISA test, extensive serological cross-reactivities are observed in all purified pilus preparations from all *B. bronchiseptica* strains. Monoclonal antibodies prepared against one preparation of *B. bronchiseptica* pill also react extensively with all other *B. bronchiseptica* pilus preparations.

Antiserum prepared against each molecular subunit species (21 Kd, 22 Kd or 24 Kd protein) reacts very strongly with the other species. This is further confirmed by immunoblotting techniques.

Any *B. bronchiseptica* strain having pill can be used as a source of immunogenic pilus subunit proteins. It is preferable to use the strain designated NADL 2-9 which was isolated by Dr. D. Croghan, USDA, National Animal Disease Laboratory, Ames, Iowa. Other exemplary strains are B133 (NVSL, USDA, Ames, Iowa), NADL 7-8 (Dr. Dave Bemis, University of Tennessee, Knoxville, Tenn.), 5389 and 5998 (Dr. Howard Hill, Iowa State University, Ames, Iowa).

ADMINISTRATION AND FORMULATION

Compositions and vaccines may be prepared using any physiologically acceptable excipient or excipients. Preferably, vaccines will be formulated with one or more excipients which have adjuvant activity. For example, the subject vaccines may be formulated with Freund's complete or incomplete adjuvant. Alternatively, mycobacterial cell wall subunit materials which have adjuvant activity such as glycodideptides, e.g. N-acetylmuramyl-L-alanyl-O-iosglutamine and its numerous derivatives and analogues, may be incorporated into the vaccine formulation. Other adjuvant excipients such as aluminum hydroxide are also useful. Various other acceptable formulations which may be used herein are known in the art, such as those set out in *Remington's Pharmaceutical Sciences,* 16th Ed., A. Osol Ed., Mack Publishing Co., Easton, PA (1980) and other texts and references on pharmaceutical and veterinary formulations.

An especially efficacious adjuvant vehicle comprises an immunopotentiating amount of a glycodipeptide, a multi-phase forming amount of a non-toxic polyoxypropylene-polyoxyethylene block copolymer, a multi-phase-stabilizing amount of a glycol ether-based surfactant, optionally a metabolizable oil, and buffered aqueous solution in a quantity sufficient to make volume.

An effective amount of immunostimulating glycopeptide is that amount which effects an increase in titer level when administered in conjunction with an antigen over that titer level observed when the glycopeptide has not been co-administered. As can be appreciated, each glycopeptide may have an effective dose range that may differ from the other glycopeptides. Therefore, a single dose range cannot be prescribed which will have a precise fit for each possible glycopeptide: however, as a general rule, the glycopeptide will preferably be present in the vaccine in an amount of between 0.001 and 5% (w/v). A more preferred amount is 0.01 to 3% (w/v).

The polyoxypropylene-polyoxyethylene (POP-POE) block polymers of this formulation are a widely available material commercially known by the trademark Pluronic ® polyols. These compounds can be prepared by the methods set out in U.S. Pat. No. 2,674,619 issued to Lunsted, incorporated herein by reference. The polymers of particular interest to this formulation are those having an average molecular weight between about 2,000 and 15,500. Such materials are commercially available from several sources, for example, BASF-Wyandotte Corp., Parsippany NJ. and E. I. Du pont.

POP-POE polyols available from BASF-Wyandotte under the name Pluronic ® are identified by a letter prefix followed by a two or a three digit number. The letter prefixes are L, P and F and refer to the physical form of each polymer, L-liquid, P-paste, or F-flakeable solid. The two and three digit numbers are used to designate the average molecular weight of the polyoxypropylene hydrophobic midsection in comparison with the percent polyoxyethylene in the total molecule. Most preferred are the polymers wherein POE comprises about 10% (w/w) of the polymer and the POP midsection has a molecular weight of about 4000 or about 3250, e.g., Pluronic ® polyols L-121 and L-101 respectively.

A multi-phase forming amount of polymer is that quantity which will form micelles, or more broadly, a system characterized as an emulsion or suspension. That amount is usually between 0.2% and 49% by volume. No more than 5% is preferred and 2.5% is most preferred.

Glycol ether derived compounds are the preferred emulsifying agents in this formulation, especially PEG 200, 300, 400, 600 and 900, and sorbitan-based non-ionic surfactants, e.g., SPAN, ARLACEL, and TWEEN ®, available commercially from ICI America's Inc. Multiphase stabilization can usually be effected by having the surfactant present in an amount of 0.05% to 2.5% by weight (w/w). An amount of 0.2% to 1% is preferred.

Immune response stimulating glycopeptides which may be used in the formulation are disclosed in U.S. Pat. Nos. 4,094,971, 4,101,536, 4,153,684, 4,235,771, 4,323,559, 4,327,085, 4,185,089, 4,082,736, 4,369,178, 4,314,998 and 4,082,735, and 4,186,194. These patents are incorporated herein by reference and made a part hereof as if set out in full herein.

Another component of these formulations, which may be present at the option of the formulator, is a metabolizable, non-toxic oil, preferably one of 6 to 30 carbon atoms including, but not limited to, alkanes, alkenes, alkynes, and their corresponding acids and alcohols, the ethers and esters thereof, and mixtures thereof. The oil may be any vegetable oil, fish oil, animal oil or synthetically prepared oil which can be metabolized by the body of the animal or bird to which the adjuvant will be administered and which is not toxic to the organism. Mineral oil and similar toxic petroleum distillate oils are expressly excluded from this invention.

The oil component of these adjuvants and vaccine formulations will be present in an amount from 1% to 30% by weight but preferably in an amount of 1% to 10% w/v. It is most preferred to use a 5% w/v concentration of oil.

The aqueous portion of these adjuvant compositions is buffered saline. Any physiologically acceptable buffer may be used herein, but phosphate buffers are preferred. Other acceptable buffers such as acetate, tris, bicarbonate, carbonate, or the like may be used as substitutes for phosphate buffers.

Adjuvant preparations are readily made by well known art methods. For example, one can make a 2-fold concentrated solution of the antigen and glycopeptide in the buffered saline. A two-fold concentration of the block polymer, oil, and multiphase stabilizing surfactant is mixed with buffered saline; then the first and second solution are mixed.

This invention is further illustrated by the non-limiting preparations and examples which follow.

EXAMPLE I

This Example illustrates one method for growing, separating and recovering the pilus subunit proteins referred to above.

*Bordetella bronchiseptica* was obtained from Dr. David Bemis, University of Tennessee, Knoxville, Tenn. The culture was originally isolated by Dr. D. Croghan, USDA, National Animal Disease Laboratory, Ames, Iowa and was designated NADL 2-9.

The purity of the strain was determined at the time master seed was prepared. The organisms were evaluated for purity using Tryptic Soy Broth and Thioglycollate Broth. The inoculated flasks were incubated for 14 days and then streaked onto blood agar plates. Representative colonies were examined for morphology and gram stained. Only colonies characterized as typical and pure cultures of *Bordetalla bronchiseptica* were selected. Biochemical analysis was conducted on isolated colonies.

Master seed cultures and working seed cultures were grown on commercially available Brucella Agar medium. Subcultures and production organisms were grown in production medium. The composition of the production medium was as follows:

| Composition of Medium | |
|---|---|
| Base Medium | |
| Tryptose | 20.0 g |
| Dextrose | 2.0 g |
| Sodium chloride | 5.0 g |
| Disodium phosphate | 2.5 g |
| Monosodium glutamate | 10.7 g |
| Deionized water qs to | 1000.0 ml |
| Supplement A | |
| L-Cystine | 4.0 g |
| Hydrochloric acid, 4N | 40.0 ml |
| Deionized water qs to | 1000.0 ml |
| Supplement B | |
| Ferrous sulfate ($FeSO_4 \cdot 7H_2O$) | 1.3 g |
| Calcium chloride ($CaCl_2$) | 2.3 g |
| Magnesium chloride ($MgCl_2 \cdot 6H_2O$) | 10.0 g |
| Deionized water qs to | 100.0 ml |
| Supplement C | |
| Ascorbic acid | 2.0 g |
| Nicotinamide | 1.0 g |
| Sodium acetate | 20.0 g |
| Deionized water qs to | 1000.0 ml |

The base medium was steam-sterilized for 15 to 45 minutes. Supplements A, B and C were filter-sterilized. 10 ml of Supplement A, 10 ml of Supplement B, and 10 ml of Supplement C were added to a liter of the base medium previously sterilized and cooled to 40°–50° C. Production medium was used within 14 days.

| Composition of Brucella Agar Medium | |
|---|---|
| Bacto-Peptamin | 20.0 g |
| Bacto-Dextrose | 1.0 g |
| Bacto-Yeast extract | 2.0 g |
| Sodium chloride | 5.0 g |
| Sodium bisulfite | 0.1 g |
| Agar | 15.0 g |
| Deionized water qs to | 1000.0 ml |

Brucella Agar Medium was steam-sterilized, dispensed into petri dishes, and used within 30 days.

Working seed cultures and subcultures were grown in 200–2000 ml flasks. Seed cultures used to inoculate the fermenter vessels were grown in 20 liter containers or seed fermenters. Production cultures were grown in 800 liter fermenter vessels.

The cultures were incubated for 10 to 48 hours under controlled conditions, with the temperature maintained at approximately 37° C. Cultures were aerated at a constant rate with filtered sterile air and/or oxygen. Dissolved oxygen was maintained at or above 80% saturation. The pH was maintained at 7.1–7.6 by additions of propionic acid 2N or sodium hydroxide 5N. Sterile antifoam solution was added as needed to control foaming, not exceeding 6 ml antifoam additive per liter of medium.

When the culture reached the desired cell growth, harvest was initiated. The culture was evaluated for typical morphology and growth density. The optical density was determined using a photometer. (At the time of the harvest, the optical density of the culture at 560 nm should be 1.5 or greater.)

Heat was used to harvest the culture. The culture was heated to approximately 60° C. for one hour under vigorous agitation and then cooled to room temperature. During this process, pill detach from the bacteria. Formalin (37% formaldehyde solution) was added to the culture to make up a final concentration of 0.2% and the culture held at room temperature for 2 or more days. Following inactivation, the culture was transferred to a sterile holding vessel. Merthiolate ® was added to the final product to a concentration of 0.01%.

The inactivated culture may be precipitated by any acceptable method, but it is preferred to use polyethylene glycol 6000 (PEG). PEG solution was added to a concentration of 3%. Sodium chloride was then added to a final concentration of 0.5M. The culture was allowed to settle for at least 24 hours at 4°–7° C. The precipitated culture was concentrated by continuous flow centrifugation using Sharples-type equipment. The sediment was then resuspended in Tris buffered saline (0.05M, pH 7.2) and diluted with an equal volume of sterile deionized water containing 0.2% formalin. The resuspended sediment containing antigen and cells was centrifuged again to remove the cells. Following continuous flow centrifugation, the supernatant containing pili was collected. Merthiolate ® was then added to 0.01% concentration.

The pill-containing supernatant was then diluted with sterile diluent, aluminum hydroxide and Merthiolate ® in the proportion needed to obtain the desired concentration of the antigen. Diluted material was assayed for antigen content by the ELISA (Enzyme Linked Immunosorbent Assay) test. The pill contents by weight were correlated with the ELISA unitage. One example of such a formulation is:

|  | UNITS/ML | VOLUME (ML) |
|---|---|---|
| Supernatant | 36 U/ml | 50.0 |
| Diluent |  | 112.0 |
| Aluminum hydroxide |  | 18.0 |
| Merthiolate ® |  | 0.18 |
| TOTAL | 10 U/ml | 180.18 ml |

The pH was then adjusted to approximately 7.2–7.6 by the addition of sodium hydroxide 5N or hydrochloric acid 4.8N, as required.

EXAMPLE II

A similar, but alternative, method for preparing and isolating the three subunit proteins is as follows:

An aliquot of *B. bronchiseptica*, strain NADL 2-9, (0.25 ml of a seed lot) was inoculated on each of 6 Brucella agar plates. These plates were incubated 24 hours at 37° C. Brucella broth, 5 ml, was added to each of the 6 agar plates. The cells were harvested from the plates and resuspended in the 5 ml of Brucella broth. 0.4 ml of the resuspended cells was inoculated for confluent growth on each of a total of 67 Brucella plates. The plates were incubated for 25 hours at 37° C. 10 ml of Tris-buffered saline, pH 7.0, was added to each of the Brucella agar plates. The cells were harvested from the plates in the buffered solution. Cell suspensions from all plates were combined.

The combined suspension was blended at 12,000 RPM for 15 minutes with an Omnimixer. Blended cells were centrifuged at 9000 RPM for 30 minutes. The supernatant was saved and the pellet discarded. 12.4 ml of 30% PEG and 11.8 ml of 4M NaCl per hundred ml of supernatant were added. The combined solutions were mixed, then refrigerated at 4° C. for 21 hours.

The antigen precipitate was pelleted by centrifugation at 11,000 RPM for 60 minutes and resuspended in 200 ml of Tris-buffered saline, pH 7.0. The antigen was solubilized by vortexing briefly and mixing for 30 minutes. The solution was clarified by centrifugation at 9000 RPM for 30 minutes. This procedure was repeated to give a protein concentrate which was then filtered through a 1.2 μm membrane filter. The three subunit proteins were determined by running this material on a SDS-PAGE system to separate the three proteins. Each protein was recovered from the acrylamide gel and serologic testing was done. The results of ELISA tests are given in Table 1.

TABLE 1
ELISA Titers of Specific Antisera Against Various Pilus Preparations of *B. bronchiseptica*.

| Antiserum | ELISA Titer | | |
|---|---|---|---|
| Antigen | Anti-21Kd | Anti-22Kd | Anti-24Kd |
| Strain B 133 | 2671 | 337 | 2242 |
| Strain 2-9 | 2623 | 445 | 2746 |
| Strain 7-8 | 2210 | 298 | 1768 |
| Strain 5389 | 2778 | 487 | 2070 |
| Strain 6126 | 2339 | 298 | 2270 |
| Strain 5598 | 2427 | 24 | 704 |
| Flagella from Strain 110 NH | 19 | 0 | 15 |

EXAMPLE III

A study was carried out to evaluate the efficacy of the *B. bronchiseptica* bacterin prepared in Example I.

The evaluation of immunogenicity was performed in host animals by vaccination of sows and/or offspring followed by challenge of the pigs. The immunogenicity was determined by comparing nasal turbinate atrophy of vaccinated and non-vaccinated pigs from vaccinated sows to the turbinate atrophy of non-vaccinated pigs from non-vaccinated control sows.

A bacterin prepared as in Example I was diluted 1:2 with a diluent containing 10% aluminum hydroxide. Immunized sows received two 2 ml intramuscular vaccinations two weeks apart. The last vaccination was administered approximately two weeks prior to farrowing. Immunized piglets received two 2 ml intramuscular vaccinations two weeks apart, at 7 and 21 days of age. Following vaccinations, sows and pigs were observed daily for 10 days for local and clinical post-vaccination reactions.

All test pigs were weaned at three weeks of age, transferred to isolation facilities, and then challenged. Pigs were kept in isolation until termination of the test. All piglets were challenged intranasally three days following second vaccination, at 24 days of age. Challenge consisted of 0.5 ml dose in each nostril with an 18 hour culture of *Bordetella bronchiseptica*, NVSL strain B-133, containing an average of $3.9 \times 10^9$ CFU/ml.

Sows were bled at the time of primary immunization, at the time of second vaccination, and at farrowing. Colostrum samples were also collected during the first 12 hours post-farrowing. Piglets were bled at challenge and at necropsy. Sera were collected and antibody titers determined by the serum agglutination test.

All pigs were sacrificed 60 days following challenge, at about 12 weeks of age. At necropsy, the snout of each pig was sectioned at the level of the first premolar tooth. The degree of turbinate atrophy was determined and scored. The scoring was based on the "Scoring system for turbinate atrophy" used at the NVSL, Ames, Iowa. The individual score of each pig and particular group was statistically analyzed by the Mann-Whitney test and the level of significance between the groups determined.

The scoring system for determination of turbinate atrophy is as follows:
- 0 = Normal turbinates
- 1 = Slight distortion of single turbinate
- 2 = Noticeable turbinate atrophy, involving only the ventral turbinates
- 3 = Progressive and severe destruction, involving both turbinates.
- 4 = Complete degeneration of turbinates accompanied by septal malformation.

Test results are summarized as follows:

Clinical Observation

Following vaccinations, local or systemic reactions attributable to vaccinations were not observed in any of the vaccinated sows and piglets.

Turbinate Atrophy Evaluation

Group I

Vaccinated pigs from vaccinated sows. 87% of the pigs (46/53) remained normal or showed only a slight to noticeable single turbinate atrophy (scoring 0, 1, and 2). Severe atrophy was observed in 13% (7/53) of the pigs (scoring 3). Complete atrophy was not observed. Mean score per pig was 1.52.

Group II

Non vaccinated pigs from vaccinated sows. Ninety-one percent of the pigs (41/45) remained normal or showed only a slight to noticeable single turbinate atrophy (scoring 0, 1, and 2). Severe atrophy was observed in 9% (4/45) of the pigs (scoring 3). Complete atrophy was not observed. Mean score per pig was 1.54.

Group III

Non-vaccinated pigs from non-vaccinated sows. Fifty-four percent of the pigs (31/58) remained normal or showed slight to noticeable turbinate atrophy (scoring 0, 1, and 2). Severe atrophy was observed in 34% (20/58) of the pigs. Only this group showed complete atrophy (scoring 4) in 12% (7/58) of the pigs. Mean score per pig was 2.32.

Serological Response

Sows

Prior to vaccination, sows of Groups I, II, and III had mean antibody titers of 15, 25, and 23, respectively. At the time of the second vaccination, approximately two weeks prior to farrowing, mean antibody titer from sows of Group I and II showed a significant increase to 1024 and 1626 respectively. Antibody titer from sows in Group III was 11.

At farrowing, mean antibody titer of Group I and Group II remained virtually unchanged—939 and 1825, respectively. Mean antibody titer of Group III also remained unchanged—12. Colostrum samples showed mean antibody titer of 2497 for Group I, 2896 for Group II, and 43 for Group III.

Pigs

At challenge, mean antibody titer of pigs from Group I (vaccinated sows, vaccinated pigs) was 284. At necropsy the titer declined to 29.

At challenge, mean antibody titer of pigs from Group II (vaccinated sow, non vaccinated pigs) was 406. At necropsy the titer declined to 24.

Mean antibody titer of pigs from Group III (non vaccinated sows, non vaccinated pigs) was 2 at challenge and 17 at necrospy.

These results demonstrate that *B. bronchiseptica* pili are effective in protecting piglets from turbinate atrophy.

EXAMPLE IV

The cross-protective activity of the 22 Kd subunit protein against *B. pertussis* induced whooping cough was determined as follows:

The 22K protein was obtained by growing two *B. bronchiseptica* strains, 5389 and NADL 2-9, for 12-16 hours on agar plates and harvesting in phosphate-buffered saline solution, pH 6.8. Cell suspensions were individually pooled and blended in a high-speed stirrer at 20,000 RPM for 5 minutes. Each suspension was then clarified by centrifugation at 12,000×g for 15 minutes and again at 24,000×g for 15 minutes.

Pili were initially purified by blending the combined suspension at 12,000 RPM for 15 minutes with an Omnimixer. Blended cells were then centrifuged at 9000 RPM for 30 minutes. The supernatant was saved and the pellet discarded. 12.4 ml of 30% PEG and 11.8 ml of 4M NaCl per hundred ml of supernatant were added. The combined solutions were mixed well, then refrigerated at 4° C. for 21 hours. Pili were pelleted by centrifugation at 12,000×g for 60 minutes. Strain 5389 gave primarily 22 Kd protein with a very minor amount (less than 10%) of 24 Kd protein. Strain NADL 2-9 gave about equal amounts of 21K and 24 Kd protein with a very minor amount (about 10%) of 22 Kd subunit protein. The molecular weight distribution of these pili subunit proteins was confirmed by SDS-PAGE.

Infant BALB/C mice were immunized intraperitoneally with 100 μl of vaccine containing 8 μg of *Bordetella bronchiseptica* pilus from one or the other of the two strains and 20 μg of aluminum hydroxide gel at 6 days of age and again at 12 days of age. Mice in the control groups were also vaccinated with either *B. pertussis* or tetanus toxoid. Seven days after the second vaccination, mice were challenged by placing the animals in an aerosol chamber for 45 minutes. (See Oda, M. J. L., et al., *J. Inf. Dis.,* 50, 823–833, (1984).) Bacterial aerosol was generated using a culture suspension of *Bordetella pertussis* strain 18323 ($2.6\times10^9$ CFU/ml). A "zero time" infectivity dose of *B. pertussis* was determined to be $1\times10^5$ CFU/mouse by counting the number of viable *B. pertussis* present in the mouse lung. Body weight gain, white blood cell count and number of survivors were monitored for 23 days post-challenge.

| Test Group | Vaccine received | Survivors/ Total | % Survivors |
|---|---|---|---|
| Noninfected control | none | 6/6 | 100 |
| Vaccinated control | Tetanus toxoid | 0/14 | 0 |
| Vaccinated control | *B. pertussis* pilus, (14 μg) | 13/13 | 100 |
| Test | *B. bronchi.* pilus strain 5389, (8 μg) | 6/7 | 86 |
| Test | *B. bronchi.* pilus strain NADL 2-9, (8 μg) | 1/6 | 17 |

Mice vaccinated with *B. bronchiseptica* pilus subunit proteins of 22 Kd at 8 μg (those treated with strain 5389-derived pili) were well protected against aerosol challenge of virulent *B. pertussis.* Those vaccinated with 21K and 24K subunit proteins with a minor amount of 22K protein showed some level of protection. Mice immunized with 8 μg of protein from strain 5389 showed levels of protection about equal to mice immunized with *B. pertussis* pilus. Mice vaccinated with pili from the 5389 strain and *B. pertussis* showed normal body weight gains and normal white blood cell counts when compared with noninfected animals.

Mice vaccinated with NADL 2-9 derived pilus protein showed moderate protection against *B. pertussis* infection. This group showed white blood cell counts and body weight gains which were intermediate to those figures for strain 5389 and *B. pertussis* treated animals and the tetanus toxoid treated animals. This indicates there is some protective protein present in the NADL 2-9 pili isolate, though greater amounts of this isolate apparently would be necessary to give full protective activity.

Vaccination of mice with tetanus toxoid, an immunologically unrelated antigen, was not protective. All animals in this group died within 16 days after exposure to *B. pertussis.*

These results demonstrate the protective immunogenicity of *Bordetella bronchiseptica* pilus against *B. pertussis* infection.

EXAMPLE V

The 22 Kd protein was purified and its amino acid composition determined as follows:

*B. bronchiseptica,* strain 5389, was grown in Brucella agar and processed to recover the pili as described in Example II. Pilus subunit proteins were further separated by SOS-PAGE and localized on the gel slab by staining with 0.25M KCl (D. Hager and R. Burgess, *Anal. Biochem.,* 109, 76–86 (1980)). Gel strips containing the 22 Kd protein were excised and passed through a syringe. The protein was eluted by soaking the gel in a small volume of buffer containing 0.1M ammonium bicarbonate and 0.1% SDS. After 3 to 12 hours of incubation at 37° C., acrylamide fragments were sedimented by low speed centrifugation and the supernatant was collected. For optimal recovery, up to four elutions were performed. Supernatants were pooled and adjusted to 0.4M ammonium bicarbonate concentration. Nine volumes of anhydrous acetone were added. Flocculent precipitates of inorganic salt-protein complexes were collected by centrifugation and dried by blowing with nitrogen. The precipitate was rehydrated with water. Protein concentration and purity of each fraction was determined by analytical SDS-PAGE. Ammonium bicarbonate was removed by lyophilization and the protein was then dissolved and hydrolyzed in 6N hydrochloric acid for 22 hours and subjected to amino acid analysis on a Beckman Amino Acid Analyzer, model 119CL.

Alternatively, the pilus subunit protein bands may be visualized by coomassie blue staining to facilitate excision. SDS and coomassie blue stain may be extracted with a solvent containing acetone, trimethylamine, acetic acid and water (Henderson, L. & E. S. Oroszlan, *Anal. Biochem.,* 93, 153–157 (1979)). Protein precipitates were collected and prepared for amino acid analysis as described in the preceding paragraph.

The amino acid composition of the 22 Kd protein was determined to be: (amino acid:number of residues per molecule of protein)

aspartic acid+asparagine:26, threonine:22, serine:15, glutamic acid+glutamate:13, proline:14, glycine:20, alanine:19, cystine/2(present but not quantitated), valine:16, methionine:01, isoleucine:13, leucine:11, tyrosine:10, phenylalanine:05, histidine:02, lysine:13, tryptophan:02, arginine:05.

Cystine is determined as the dimeric form: here, cystine dimers were detected but the number per protein molecule was not determined.

EXAMPLE VI

A vaccine is prepared as follows:

| Solution I | | |
|---|---|---|
| Sodium Chloride (NaCl) | | 80.0 g |
| Potassium Chloride (KCl) | | 2.0 g |
| Potassium Phosphate (KH$_2$PO$_4$) | | 2.0 g |
| Dibasic Sodium Phosphate (Na$_2$HPO$_4$·7H$_2$O) | | 21.6 g |
| Tween 80 | | 40.0 ml |
| Distilled water q.s. | | 10,000.0 ml |
| Solution II | | |
| N—acetyl-D-muramyl-L-threonyl-D-isoglutamine | | 0.6 g |
| Solution I | | 50.0 ml |
| Complete adjuvant asssembly | | |
| | Percent | |
| Solution I | 84.5 | 8,450.0 ml |
| Solution II | 0.5 | 50.0 ml |
| Squalene | 10.0 | 1,000.0 ml |
| Pluronic ® L-121 | 5.0 | 500.0 ml |

The final vaccine is formulated by mixing one part pili-containing supernatant (see Example I) with one part of the adjuvant assembly.

What is claimed is:

1. A vaccine for immunizing a human subject against *Bordetella pertussis* which comprises an effective amount of an antigen consisting essentially of a pilus subunit protein from *Bordetella bronchiseptica* characterized by having a molecular weight of about 22,000 daltons as determined by sodium dodecyl sulfate-polyacrylamide gel electrophoresis and having the amino acid composition (amino acid:number of residues per molecule of protein): aspartic acid/asparagine:26, threonine:22, serine:15, glutamic acid/glutamate:13, proline:14, glycine:20, alanine:19, cystine/2:present, valine:16, methionine:1, isoleucine:13, leucine:11, tyrosine:10, phenylalanine:5, histidine:2, lysine:13, tryptophan:2, and arginine:5.

2. The vaccine of claim 1, further comprising an adjuvant.

3. A substantially pure pilus subunit protein from *Bordetella bronchiseptica* characterized by having a molecular weight of about 22,000 daltons as determined by sodium dodecyl sulfate-polyacrylamide gel electrophoresis and having the amino acid composition (amino acid:number of residues per molecule of protein): aspartic acid/asparagine:26, threonine:22, serine:15, glutamic acid/glutamate:13, proline:14, glycine:20, alanine:19, cystine/2:present, valine:16, methionine:1, isoleucine:13, leucine:11, tyrosine:10, phenylalanine:5, histidine:2, lysine:13, tryptophan:2, and arginine:5.

4. A vaccine for immunizing a human subject against *Bordetella pertussis* which comprises:

an immunologically effective amount of an antigen consisting essentially of a pilus subunit protein from *Bordetella bronchiseptica* characterized by having a molecular weight of about 22,000 daltons as determined by sodium dodecyl sulfate-polyacrylamide gel electrophoresis and having the amino acid composition (amino acid:number of residues per molecule of protein):

aspartic acid/asparagine:26, threonine:22, serine:15, glutamic acid/glutamate:13, proline:14, glycine:20, alanine:19, cystine/2:present, valine:16, methionine:1, isoleucine:13, leucine:11, tyrosine:10, phenylalanine:5, histidine:2, lysine:13, tryptophan:2, and arginine:5;

an effective amount of an immunostimulating glycopeptide;

a multi-phase-forming amount of a non-toxic polyoxypropylene-polyoxyethylene block polymer;

a multi-phase-stabilizing amount of a glycol ether-based surfactant; and buffered saline.

5. The vaccine of claim 4 comprising 0.0001–15% w/v immunostimulating glycopeptide;

0.2–20% v/v multi-phase-forming, non-toxic polyoxypropylene-polyoxyethylene block polymer;

0.05–2.5% v/v multi-phase-stabilizing glycol ether-based surfactant; and phosphate-buffered saline.

6. The vaccine of claim 5 wherein said glycopeptide is

N-acetylmuramyl-L-α-aminobutyryl-O-isoglutamine;

6-O-stearoyl-N-acetylmuramyl-L-α-aminobutyryl-D-isoglutamine;
N-acetylmuramyl-L-threonyl-O-isoglutamine;
N-acetylmuramyl-L-valyl-O-isoglutamine;
N-acetylmuramyl-L-alanyl-D-isoglutamine;
N-acetyl-desmethylmuramyl-L-alanyl-O-isoglutamine;
N-acetylmuramyl-L-alanyl-O-glutamine n-butyl ester;
N-acetylmuramyl-L-seryl-O-isoglutamine;
N-acetyl(butylmuramyl)-L-α-aminobutyryl-O-isoglutamine; or
N-acetyl(butylmuramyl)-L-alanyl-D-isoglutamine.

7. The vaccine of claim 6 wherein:
said glycopeptide is N-acetylmuramyl-L-threonyl-D-isoglutamine present in an amount of 0.03% w/v; and
said block polymer has a polyoxypropylene midsection of molecular weight between 3,250 and 4,000 and the percent polyoxyethylene in the block polymer comprises 0.2 to 20% w/w.

8. A method for immunizing a human subject against B. pertussis which method comprises vaccinating a human subject with a composition comprised of an effective amount of inactivated B. bronchiseptica having pili in a pharmaceutically acceptable excipient.

9. The method of claim 8 wherein the pharmaceutically acceptable excipient is an adjuvant.

10. The method of claim 9 wherein the adjuvant comprises:
an effective amount of an immunostimulating glycopeptide;
a multi-phase-forming amount of a non-toxic polyoxypropylene-polyoxyethylene block polymer;
a multi-phase-stabilizing amount of a glycol ether-based surfactant; and
buffered saline.

11. The method of claim 10 which comprises
0.0001–15% w/v immunostimulating glycopeptide;
0.2–20% v/v multi-phase-forming, non-toxic polyoxypropylene-polyoxyethylene block polymer;
0.05–2.5% v/v multi-phase-stabilizing glycol ether-based surfactant; and
phosphate-buffered saline.

12. The method of claim 11 wherein said glycopeptide is
N-acetylmuramyl-L-α-aminobutyryl-D-isoglutamine;
6-O-stearoyl-N-acetylmuramyl-L-α-aminobutyryl-D-isoglutamine;
N-acetylmuramyl-L-threonyl-D-isoglutamine;
N-acetylmuramyl-L-valyl-D-isoglutamine;
N-acetylmuramyl-L-alanyl-D-isoglutamine;
N-acetyl-desmethylmuramyl-L-alanyl-D-isoglutamine;
N-acetylmuramyl-L-alanyl-D-glutamine n-butyl ester;
N-acetylmuramyl-L-seryl-D-isoglutamine;
N-acetyl(butylmuramyl)-L-α-aminobutyryl-D-isoglutamine; or
N-acetyl(butylmuramyl)-L-alanyl-D-isoglutamine.

13. The method of claim 12 wherein:
said glycopeptide is N-acetylmuramyl-L-threonyl-D-isoglutamine present in an amount of 0.03% w/v; and
said block polymer has a polyoxypropylene midsection of molecular weight between 3,250 and 4,000 and the percent polyoxyethylene in the block polymer comprises 0.2 to 20% w/w.

14. A method for immunizing a human subject against B. pertussis which method comprises vaccinating a human subject with a composition comprised of substantially pure pilus protein derived from B. bronchiseptica in a pharmaceutically acceptable excipient.

15. The method of claim 14 wherein said protein is a pilus subunit protein which has a molecular weight of about 22 Kd as determined by SDS-PAGE and has the amino acid composition:
aspartic acid/asparagine:26, threonine:22, serine:15, glutamic acid/glutamate:13, proline:14, glycine:20, alanine:19, cystine/2:present, valine:16, methionine:1, isoleucine:13, leucine:11, tyrosine:10, phenylalanine:5, histidine:2, lysine:13, tryptophan:2, and arginine:5.

16. The method of claim 15 wherein the pharmaceutically acceptable excipient is an adjuvant.

17. The method of claim 16 wherein the adjuvant comprises:
an effective amount of an immunostimulating glycopeptide;
a multi-phase-forming amount of a non-toxic polyoxypropylene-polyoxyethylene block polymer;
a multi-phase-stabilizing amount of a glycol ether-based surfactant; and
buffered saline.

18. The method of claim 17 which comprises
0.0001–15% w/v immunostimulating glycopeptide;
0.2–20% v/v multi-phase-forming, non-toxic polyoxypropylene-polyoxyethylene block polymer;
0.05–2.5% v/v multi-phase-stabilizing glycol ether-based surfactant; and
phosphate-buffered saline.

19. The method of claim 18 wherein said glycopeptide is
N-acetylmuramyl-L-α-aminobutyryl-D-isoglutamine;
6-O-stearoyl-N-acetylmuramyl-L-α-aminobutyryl-D-isoglutamine;
N-acetylmuramyl-L-threonyl-D-isoglutamine;
N-acetylmuramyl-L-valyl-D-isoglutamine;
N-acetylmuramyl-L-alanyl-D-isoglutamine;
N-acetyl-desmethylmuramyl-L-alanyl-D-isoglutamine;
N-acetylmuramyl-L-alanyl-D-glutamine n-butyl ester;
N-acetylmuramyl-L-seryl-D-isoglutamine;
N-acetyl(butylmuramyl)-L-α-aminobutyryl-O-isoglutamine; or
N-acetyl(butylmuramyl)-L-alanyl-D-isoglutamine.

20. The method of claim 19 wherein:
said glycopeptide is N-acetylmuramyl-L-threonyl-D-isoglutamine present in an amount of 0.03% w/v; and
said block polymer has a polyoxypropylene midsection of molecular weight between 3,250 and 4,000 and the percent polyoxyethylene in the block polymer comprises 0.2 to 20% w/w.

* * * * *